US010456565B2

(12) United States Patent
Rosenbaum et al.

(10) Patent No.: US 10,456,565 B2
(45) Date of Patent: Oct. 29, 2019

(54) LOCKING LOOP CATHETER

(71) Applicant: Cook Medical Technologies LLC, Bloomington, IN (US)

(72) Inventors: Joanna Lynn Rosenbaum, Northbrook, IL (US); Andrea Christine Lawrence Mydosh, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 765 days.

(21) Appl. No.: 14/988,866

(22) Filed: Jan. 6, 2016

(65) Prior Publication Data

US 2016/0199625 A1    Jul. 14, 2016

Related U.S. Application Data

(60) Provisional application No. 62/102,909, filed on Jan. 13, 2015.

(51) Int. Cl.
*A61M 27/00* (2006.01)
*A61M 25/00* (2006.01)
(Continued)

(52) U.S. Cl.
CPC ........ *A61M 27/00* (2013.01); *A61M 25/0071* (2013.01); *A61M 25/0147* (2013.01); *A61M 25/04* (2013.01); *A61M 2025/0163* (2013.01)

(58) Field of Classification Search
CPC .............. A61M 27/00; A61M 25/0071; A61M 25/0147; A61M 25/04; A61M 25/0041; A61M 2025/163
See application file for complete search history.

(56) References Cited

U.S. PATENT DOCUMENTS 3,119,392 A * 1/1964 Zeiss .................... A61B 17/221
                                                604/95.04
4,752,092 A * 6/1988 Faust .................... E05B 83/24
                                                   292/201
(Continued)

FOREIGN PATENT DOCUMENTS

DE       94 09 072.6      10/1994
EP       1 803 481 A2      4/2007
(Continued)

OTHER PUBLICATIONS

European Search Report for EP 17 20 1557, dated Feb. 21, 2018, 11 pp.

(Continued)

*Primary Examiner* — Ariana Zimbouski
(74) *Attorney, Agent, or Firm* — Brinks Gilson & Lione

(57) ABSTRACT

A drainage catheter system includes an elongate tube with proximal and distal ends and a filament extending the tube that is adjustable to create a closed loop at the distal end of the tube when the filament is retracted relative to the tube. The filament is coupled to the tube such that the filament and tube are prevented from being separated in the event that the tube and filament are cut at the proximal end at the conclusion of a drainage procedure. The filament can be attached to the tube near the distal end. The filament can be attached to the tube along its length. The catheter system can also include a retraction mechanism having a first fixed position and second fixed position, where the second fixed position retracts the filament proximally relative to the first fixed position by actuating a plunger.

12 Claims, 6 Drawing Sheets

(51) Int. Cl.
*A61M 25/01* (2006.01)
*A61M 25/04* (2006.01)

(56) References Cited

U.S. PATENT DOCUMENTS

| | | |
|---|---|---|
| 6,508,789 B1 * | 1/2003 | Sinnott et al. |
| 2004/0039339 A1 * | 2/2004 | Magnusson ........... A61M 25/04 604/170.03 |
| 2009/0182268 A1 | 7/2009 | Thielen et al. |
| 2011/0098682 A1 | 4/2011 | Ahmed et al. |
| 2013/0103004 A1 | 4/2013 | Gray et al. |

FOREIGN PATENT DOCUMENTS

| | | |
|---|---|---|
| EP | 2 65 796 A1 | 10/2013 |
| GB | 2497286 A | 6/2013 |
| WO | WO 2007/021490 A2 | 2/2007 |
| WO | WO 2008/021596 A1 | 2/2008 |
| WO | WO 2009/089038 A1 | 7/2009 |

OTHER PUBLICATIONS

Extended European Search Report for EP 16 15 0644, dated Aug. 24, 2016, 13 pp.
Partial European Search Report for App. No. EP 16 15 0644.9, dated May 13, 2016, 5 pp.

* cited by examiner

LOCKING LOOP CATHETER

CROSS-REFERENCE TO RELATED APPLICATIONS

This application claims priority from U.S. Provisional Application No. 62/102,909, filed on Jan. 13, 2015, the entirety of which is hereby fully incorporated by reference herein.

BACKGROUND

1. Technical Field

The present invention relates to catheters and, more particularly, to locking loop drainage catheters.

2. Description of the Related Art

Locking loop drainage catheters are well known in the art. A traditional locking loop catheter includes a hub at a proximal end with an outlet port for draining the contents of the vessel in which the catheter is deployed. A flexible tube extends distally from the hub, with the tube including a lumen extending from a proximal end of the tube to the distal end of the tube. Drainage fluid flows through the lumen toward the hub. The catheter is held in place by manipulating the distal end of the tube to create a looped portion.

To manipulate the distal end of the catheter, a fixed end of a suture is attached to the hub, and the suture extends distally through the tube lumen. The suture extends through a side port of the tube near the distal end of the tube, such that the suture is disposed outside of the tube lumen. The suture re-enters the lumen through another side port and then extends proximally back toward the hub, where a free end of the suture can be adjusted.

To create the loop to lock the catheter, the free end of the suture is pulled proximally relative to the hub and tube. Pulling on the free end shortens the length of the suture that remains disposed within the tube, which moves the two side ports close together and loops the distal end of the catheter. With the free end of the suture retracted, the suture is locked to the hub to keep the catheter in a locked position.

However, locking the free end of the suture is time consuming and cumbersome. Accordingly, unlocking the suture is similarly time-consuming and cumbersome. Many surgeons will elect to simply cut off the hub at the completion of the draining procedure and when the catheter is no longer needed. With the hub cut off, the suture has free ends and is no longer in tension, and the tube will resiliently return to a generally non-looped state, allowing for retrieval of the tube out of the patient.

However, during the period where the catheter is deployed in the body, the suture can become stuck to tissue in the area. When the cut catheter is removed, the suture can ultimately be left behind in the body.

Additionally, as the free end of the suture must extend out of the hub and be retractable while also extending through the lumen, fluid in the tube lumen can sometimes leak from the location where the free end of the suture protrudes, which is undesirable.

Thus, improvements to locking loop drainage catheters can be made.

SUMMARY

A catheter is provided having a proximal end and a distal end. The catheter includes an elongate tube having a proximal end and a distal end and defining at least one lumen extending therebetween; an exit port defined by the tube and extending through the tube adjacent the distal end of the tube; an entry port extending through the tube and creating fluid communication between an exterior of the tube and the at least one lumen of the tube; and a filament extending within the elongate tube and extending out of the exit port such that a portion of the filament is exposed to the exterior of the tube and further extending into the entry port.

The filament includes a free end disposed at the proximal end, the free end being adjustable proximally and distally, wherein proximal retraction of the filament puts the filament in tension and creates a looped end portion of the tube where the exit port and entry port are urged toward each other, and releasing the filament from its proximal retraction allows the tube to return to a non-looped shape and the exit and entry ports to move away from each other. The filament is coupled to the tube to prevent the filament and tube from being separated in response to retraction of the tube.

In another aspect, the filament includes a distal secured end that is coupled to the tube at the entry port. In another aspect, the free end is disposed at an opposite end of the filament from the distal secured end. In yet another aspect, the distal secured end is disposed within the lumen of the catheter. In another aspect, the distal secured end includes a head portion having a width that is larger than a width of the entry port. In one form, the distal secured end is bonded to the tube.

In one approach, the head portion is knot. In another approach, the head portion is in the form of a T-tip.

In another aspect, the filament includes a secured length portion that is secured to the tube along a length of the tube. In one approach, the secured length portion is embedded in a sidewall of the tube. In another form, the secured length portion is disposed within the at least one lumen, and the secured length portion is bonded to an inner surface of the tube.

In another aspect, the at least one lumen comprises a drainage lumen and a filament lumen, and the filament extends through the filament lumen and exits the filament lumen at the exit port.

In one approach, the filament includes an adjustable portion that extends proximally from the entry port through the at least one lumen.

In another embodiment, a catheter system is provided that includes an elongate tube having a proximal end and a distal end and defining at least one lumen extending therebetween; an exit port defined by the tube and extending through the tube adjacent the distal end of the tube; an entry port extending through the tube and creating fluid communication between an exterior of the tube and the at least one lumen of the tube; and a filament extending within the elongate tube and extending out of the exit port such that a portion of the filament is exposed to the exterior of the tube and further extending into the entry port and proximally through the tube.

The filament includes a fixed proximal end and an adjustable free end disposed at an end opposite the fixed proximal end, the free end being adjustable proximally and distally, wherein proximal retraction of the free end puts the filament in tension and creates a looped end portion of the tube where the exit port and entry port are urged toward each other, and releasing the filament from its proximal retraction allows the tube to return to a non-looped shape and the exit and entry ports to move away from each other.

The free end of the filament is fixedly coupled to a retraction mechanism, the retraction mechanism moveable between a first fixed position and a second fixed position.

The second fixed position places the filament in tension and is disposed proximally relative to the first fixed position.

In one aspect, the retraction mechanism includes a spring that is compressed in the first position relative to the second position, and the spring biases the retraction mechanism toward the second position when compressed.

In another aspect, the retraction mechanism includes a distal cam and a proximal cam, the distal cam coupled to the free end of the filament and the spring, and the proximal cam is actuatable to move the distal cam between the first and second positions.

In one approach, the proximal cam includes a depressible plunger coupled thereto.

In another aspect, the system further includes a proximal hub coupled to the tube, and the fixed end is coupled to the hub.

In yet another aspect, the at least one lumen comprises a filament lumen and a drainage lumen, the filament extending distally from the fixed proximal end through the filament lumen and proximally through the drainage lumen after entering through the entry port.

In an additional embodiment, a catheter system is provided that includes an elongate tube having a proximal end and a distal end and defining at least one lumen extending therebetween; an exit port defined by the tube and extending through the tube adjacent the distal end of the tube; an entry port extending through the tube and creating fluid communication between an exterior of the tube and the at least one lumen of the tube, and a filament extending within the elongate tube and extending out of the exit port such that a portion of the filament is exposed to the exterior of the tube and further extending into the entry port.

The filament includes a free end disposed at the proximal end, the free end being adjustable proximally and distally, wherein proximal retraction of the filament puts the filament in tension and creates a looped end portion of the tube where the exit port and entry port are urged toward each other, and releasing the filament from its proximal retraction allows the tube to return to a non-looped shape and the exit and entry ports to move away from each other. The filament is coupled to the tube to prevent the filament and tube from being separated in response to retraction of the tube.

A retraction mechanism is coupled to the free end of the filament for adjusting the filament proximally and distally, the retraction mechanism moveable between a first fixed position and a second fixed position. The second fixed position places the filament in tension and is disposed proximally relative to the first fixed position.

DETAILED DESCRIPTION

Figure 1:
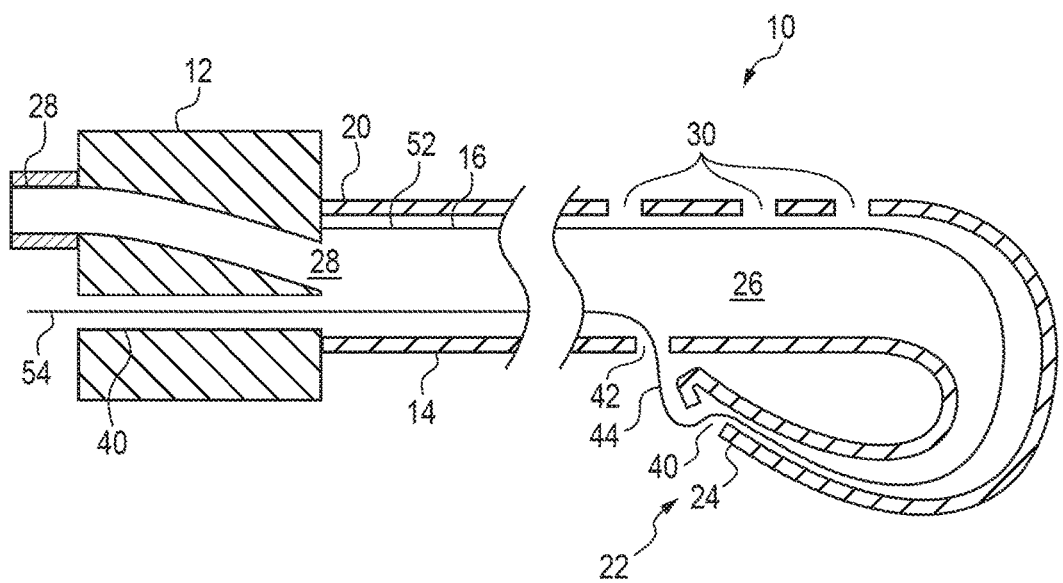
FIG. 1 is a schematic cross-sectional view of a catheter system having a hub, and elongate tube defining a lumen, and a filament extending through the tube.

Referring now to the drawings, FIGS. 1-10 illustrate a medical device or catheter 10 for use in a variety of medical applications involving the draining of fluids. The catheter 10 may include a proximal hub 12 and a tube 14 extending distally away from the hub 12. The catheter 10 further includes a filament 16 extending through the tube 14, where it exits and re-enters the tube 14 near a distal end 22 thereof. The filament 16 is retractable and lockable to create a loop at the distal end of the tube 14. The loop assists in limiting migration of the catheter 10 when deployed within a patient.

In one embodiment, the filament 16 may in the form of a suture constructed in a manner known in the art. The filament material can be any biocompatible suture material commonly used in locking loop catheters. The filament material is preferably strong enough to withstand the tensile forces created when pulled by a surgeon or other user, and flexible enough to be able to conform to the tortuous body anatomy in which it is intended to be used. The filament 16 can be in the form of a solid wire, a braided wire, a coiled wire, or other known wire type. Accordingly, the filament 16 can be either a monofilament or multifilament structure. It will be appreciated that other known suture or filament types may be used in other embodiments.

With reference to FIG. 1, the tube 14 has a proximal end 20 and a distal end 22. The proximal end 20 may be attached to the hub 12. In one embodiment, the distal end 22 may include a tapered distal tip 24. However, other shapes of the distal tip 24 may also be used, such as a blunt tip, rounded tip, or the like. The tube 14 defines a drainage lumen 26 extending from the proximal end 22 distally toward the distal tip 24. The drainage lumen 26 includes a proximal opening 28 that is in fluid communication with the hub 12, such that fluid draining through the drainage lumen 26 will flow into the hub 12. More particularly, the hub 12 includes a drainage outlet that is within the proximal opening that is in fluid communication with the drainage lumen 26, such that a fluid collection device (not shown) can be attached to the proximal opening 28 to collect fluid draining from the catheter 10. It will be appreciated that other shapes and structures may be used in place of the hub in some embodiments.

The tube 14 preferably includes a plurality of drainage inlet ports 30 in the form of side ports that define openings through side of the tube 14 to create fluid communication between the drainage lumen 26 and areas external to the catheter 10. The ports 30 are preferably disposed adjacent the distal end 22 of the tube 14. Thus, fluid in the area of the ports 30 in the body vessel to be drained will flow through the ports 30 into the drainage lumen 26, and proximally toward the hub 12 where the fluid will ultimately exit the hub 12. However, it will be appreciated that the ports 30 can also be disposed at other locations along the tube 14. The ports 30 can have various shapes and sizes known in the art. For example, the ports 30 may be circular, ovular, polygonal, slits, or the like, so long as fluid can flow therethrough.

The tube 14 also includes filament exit port 40 and filament entry port 42, each in the form of side ports. In another approach, one of the ports 40 or 42 could be through the end of the tube 14. The ports 40 and 42 are disposed near the distal end 22 of the tube 14. The filament 16 that extends through the tube 14 exits the tube 14 through the exit port 40, where the filament 16 is exposed. The filament 16 re-enters the tube 14 through the entry port 42. The portion of the length of the filament 16 that is exposed outside of the tube 14 between the exit port 40 and entry port 42 can be described as a slack portion 44. The slack portion 44 is thereby defined by the exit port 40 and entry port 42, and the slack portion 44 shortens as the filament 16 is put in tension. Shortening of the slack portion 44 causes the exit port 40 and entry port 42 to be urged together, resulting in a curved shape at the distal end 22 of the tube 14, where the curved shape will define a loop in response to increased shortening of the slack portion 44. It will be appreciated that the ports 40 and 42 may not be fully urged toward each other such that they make contact with each other; however, if the filament 16 is pulled tight enough, the ports 40 and 42 may ultimately touch each other.

In one approach, the filament 16 may extend through the drainage lumen 26, such that the exit port 40 and entry port 42 are in fluid communication with the drainage lumen 26, similar to ports 30.

Figure 2:
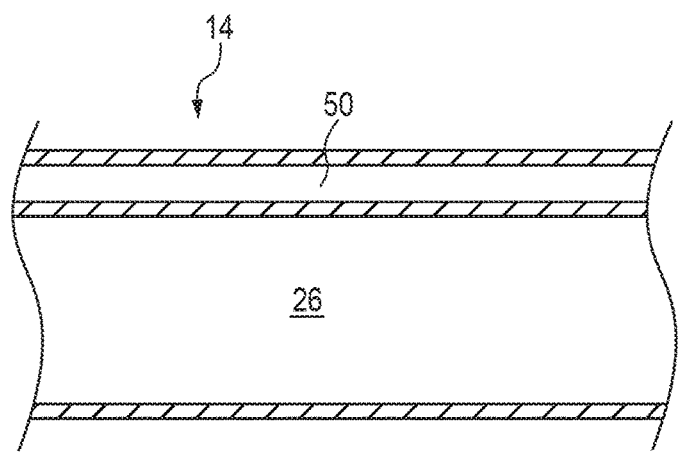
FIG. 2 is a partial cross-section view illustrating a drainage lumen and a filament lumen.

In another approach, and with reference to FIG. 2, the tube 14 may include a filament lumen 50 that extends from the proximal end 20 of the tube 14 distally toward the distal end 22 of the tube 14. The filament lumen 50 is typically smaller in diameter than the drainage lumen 26, because the filament lumen 50 only carries the filament 16 and fluid flow through the filament lumen 50 does not occur. Accordingly, the drainage lumen 26 can remain relatively large to accommodate the desired drainage flow. However, the filament lumen 50 could also be the same size or larger than the drainage lumen in another embodiment. In instances where a filament lumen 50 is used, the exit port 40 creates fluid communication between the exterior and the filament lumen 50, with the entry port 42 providing access into the drainage lumen 26. In an alternative approach, the entry port 42 could provide access back into the filament lumen 50, or into a further lumen (not shown).

The filament 16 may include a fixed end 52 and an adjustable end 54. The fixed end 52 can be fixed to various locations of the catheter 10. The adjustable end 54 preferably extends out of the hub 12 to a locking mechanism 60 (further described below). The fixed end 52 may be fixed via adhesive, heat bonding, or other known methods for secure attachment, some of which will be further detailed below. The adjustable end 54 is arranged at the hub 12 to allow a user to manipulate or retract the filament 16 and its length that extends through the catheter 10. For example, the adjustable end 54 can be pulled or otherwise retracted relative to the hub 12, which results in a shortening of the length of the filament 16 that extends through the tube 14. As the length is decreased, the slack portion 44 is also decreased. This shortening of the slack portion 44 causes the exit port 40 and entry port 42 to be urged together to create the looped or curved distal end 22 of the tube 14.

As described above, the filament 16 extends out of the tube 14 and back into the tube 14 near the distal end 22 of the tube 14. In one approach, the fixed end 52 is fixed at the proximal end 20 of the tube 14, either to the hub 12 or the tube 14. The filament 16 extends along the length of the tube 14 through either the drainage lumen 26 or the filament lumen 50. The exit port 40 is, in one approach, located distally from the entry port 42. Thus, the filament 16 reaches the exit port 40 and exits the tube 14, where it is routed back proximally and toward the entry port 42, where it reenters the tube 14. However, in another approach, the exit port 40 could be located proximally from the entry port 42, where the filament 16 continues to extend proximally outside of the tube 14 before reaching the entry port 42.

The filament 16 then extends proximally from the entry port 42 back toward the hub 12, where the adjustable end 54 is made available for adjustment by the user. Thus, in this approach, the lumen 26 or 50 includes two portions of the filament 16 side-by-side along the length of the tube 14 proximal of the entry port 42. In the case of a dual lumen design, the portions of the filament 16 are separated by the wall the separates the filament lumen 50 and the drainage lumen 26.

The adjustable end 54 of the filament 16 is adjustable in order to adjust the shape of the distal end 22 of the tube 14, as described above, by urging the exit port 40 and entry port 42 toward each other in response to tension in the filament 16. More particularly, the adjustable end 54 is retractable to put the filament 16 in tension and shorten the slack portion 44. The filament 16 is put in tension in response to being retracted because the opposite end, the fixed end 52, is fixed and resists the tensile forces in the filament 16 that result from retraction. With the filament 16 in tension and shortened, the distal end 22 of the tube 14 is put in a tight loop configuration.

It is preferable for the adjustable end 54 to be easily adjustable so that adjusting the shape of the distal end 22 of the tube 14 can be performed quickly and easily. This applies to both creating the loop at the distal end 22 as well as releasing the loop at the distal end 22. By making adjustment of the adjustable end 54 fast and easy, both to put the filament 16 in tension and to release the filament 16 from tension, instances of surgeons electing to cut the tube 14 at the end of a procedure to release the tight loop at the distal end 22 are reduced.

Figure 3:
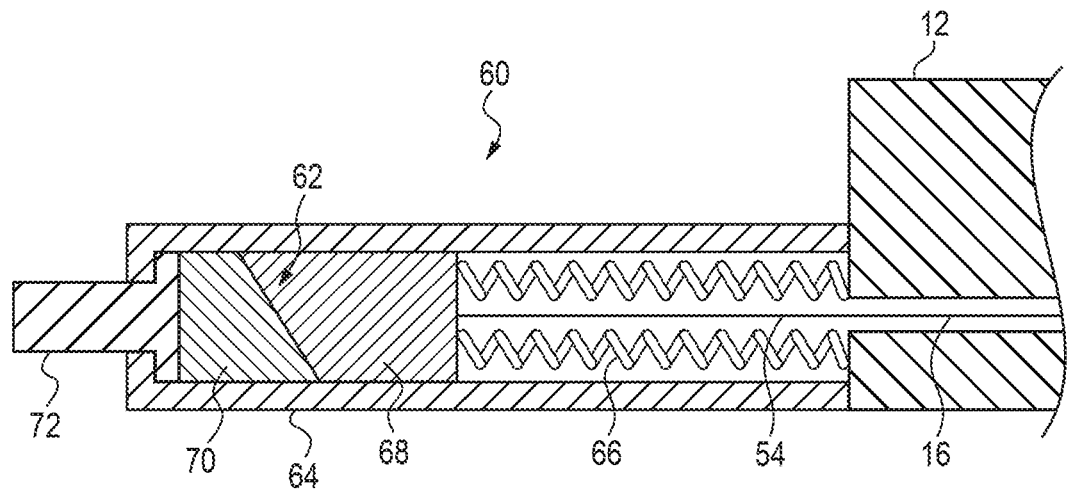
FIG. 3 is a schematic cross-sectional view showing a retraction mechanism for retracting the filament in a proximally retracted position.
Figure 4:
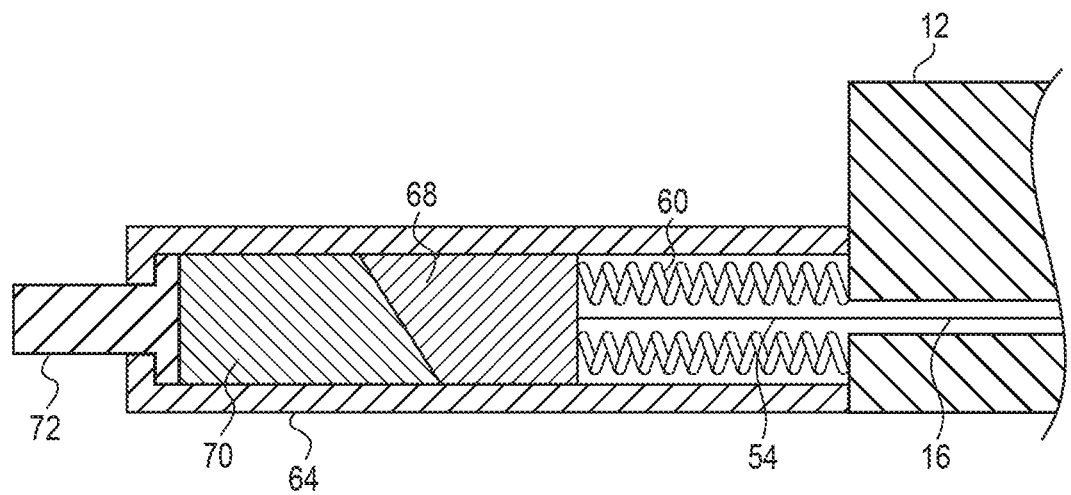
FIG. 4 is a schematic cross-sectional view showing the retraction mechanism in a distal non-retracted position.

Accordingly, and with reference to FIGS. 3 and 4, in one approach, the hub 12 can include the retraction mechanism 60. The retraction mechanism 60 can be in the form of a bi-stable cam system 62 similar in style to a typical retractable pen mechanism. The cam system 62 has two positions, each of which are maintainable once actuated, thereby making the system bi-stable. A first, distal position (FIG. 4) allows the filament 16 to be free from retracted tension in the proximal direction. A second, proximal position (FIG. 3) puts the filament 16 in tension. Each of the first and second positions are fixed positions. The cam system 62 may include a generally cylindrical tubular housing 64. Within the housing 64 a spring 66 may be disposed at the distal end 22 thereof that, when compressed, will be biased in the proximal direction. The spring 66 is loaded with potential energy when it is in the first, distal position. The size, shape, and length of the spring can be selectable to suit the particular desired tension force in the filament 16 as well as the desired length of retraction, depending on the needs of the particular application. In another embodiment, the spring 16 could be replaced by another biasing mechanism.

The cam system may include a distal cam 68 that is operatively coupled to the filament 16. The distal cam 68 is biased proximally by the spring 66. The cam system 62 may include a proximal cam 70, which can be operatively coupled to a plunger member 72 or other user-engagable member that is pushable by the user. The proximal cam 70 is translatable proximally and distally within the housing 64 to move the distal cam 68 between the first and second positions.

Similar to a retractable pen mechanism, pressing down on the proximal cam 70 via the plunger member 72 will cause the distal cam 68 to move against the spring 66 and against the bias of the spring, where the distal cam 68 will become locked in the distal position. Pressing down again on the proximal cam 70 will cause the distal cam 68 to become unlocked, and the proximal bias in the spring 66 will force the distal cam 68 proximally.

The adjustable end 54 of the filament 16 is ultimately coupled to the distal cam 68. Accordingly, when the distal cam 68 moves proximally, the filament 16 will be put in tension, thereby retracting the filament 16 proximally and shortening the length of the slack portion 44 and ultimately creating the tight loop at the distal end 22 of the tube 14.

Thus, the catheter 10 and the retraction mechanism 60 can be put in the first, distal position with the spring 66 being loaded with potential energy prior to insertion by simply pressing down on the plunger 72 to engage the first position. With the catheter 10 in place, the plunger 72 can be pressed to release the distal cam 68 from the first position, thereby pulling on the filament 16. At the conclusion of the procedure, and with the catheter 10 ready for removal, the tension in the filament 16 that creates the looped distal end 22 can be quickly and easily released by pressing the plunger 72 again. It will be appreciated that various other dual fixed position mechanisms could also be used, such as a solenoid actuated mechanism.

Accordingly, there is no need for the surgeon to untie the filament 16 or release the filament 16 from a more complex form of retention that includes time consuming release procedures. The surgeon will have no need or desire to locate a cutting instrument to cut the filament 16 to release it, because the surgeon need only press the plunger 72 to release the filament 16. Advantageously, the filament 16 remains fixed to the catheter 10 via its attachment at the fixed end 52, and the adjustable end 54 remains connected to the release mechanism. Thus, there is no danger of the filament 16 being left behind in the patient if the catheter 10 is not cut, and the desire for cutting is greatly reduced due to the simplicity of both creating and releasing the tension in the filament 16.

However, given the current practice of surgeons where the catheter 10 is cut, it is possible that some surgeons will continue to cut the catheter 10 prior to removing it from the patient.

With reference to FIGS. 5-10, in order to protect against instances where the catheter 10 is cut, the filament 16 can be attached to the tube 14 in such a way as to retain the filament 16 even after instances where the catheter 10 is cut. This attachment to the tube 14, which occurs at least distally from the location where the tube 14 is typically cut, will prevent the filament 16 from being fully removable from the distal end 22 of the catheter 10. This type of attachment can provide assurance and peace of mind to the surgeons and other users that the filament 16 will not be left behind.

As described above, the tube 14, in one embodiment, may have a dual lumen design, with the drainage lumen 26 and the filament lumen 50 extending side-by-side. The drainage lumen 26 is preferably wider than the filament lumen 50, as previously described, but could be the same size or smaller in some embodiments. The filament 16 extends distally through the filament lumen 50, where it will ultimately exit at or near the distal tip of the catheter 10, where the filament 16 will be exposed outside of the catheter 10.

Figure 5:
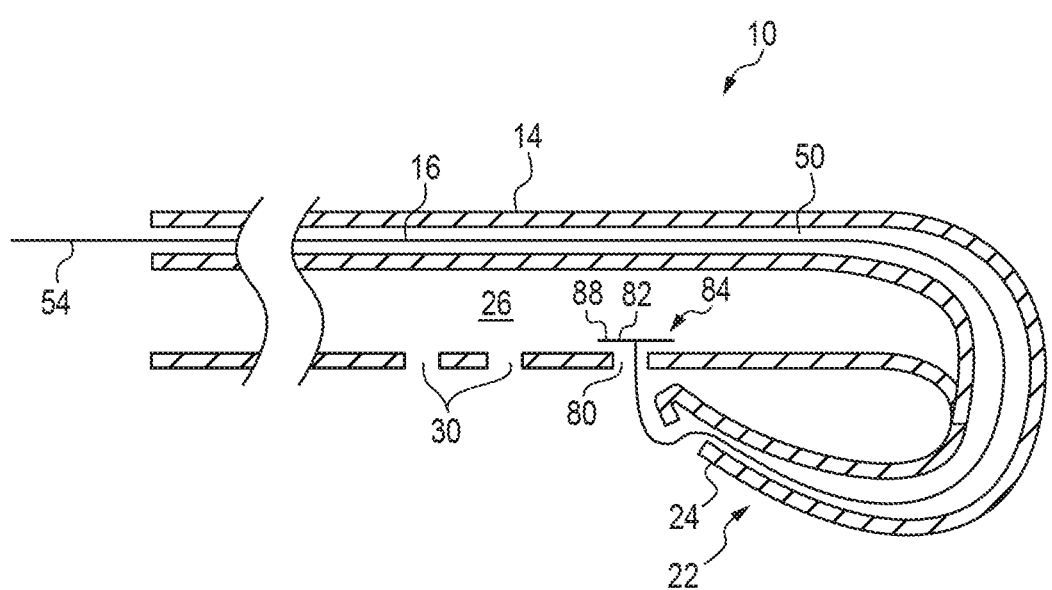
FIG. 5 is a schematic cross-sectional view of the elongate tube and the filament, with the filament attached to the tube at a distal end.

With reference to FIG. 5, in another embodiment, unlike the above described approach with a fixed proximal end and an adjustable proximal end, the filament 16 will have only one proximal end, which is the adjustable end 54. The fixed end of the filament 16 is disposed near the distal tip of the tube 14, which is further described below.

The filament 16 will extend distally through the tube 14 from the adjustable end 54 and the exposed portion of the filament 16 will loop back proximally from its exit port 40 at or near the distal tip 24. The filament 16 will then re-enter the catheter 10 via a securement port 80 that is disposed in the side of the catheter 10 at a location proximal of the exit port 40. The securement port 80 is preferably disposed through the side of the tube 14 such that it creates fluid communication between the exterior of the catheter 10 and the drainage lumen 26. Accordingly, the securement port can also provide a fluid passageway into the drainage lumen that is addition to the ports 30 described above. Moreover, the drainage lumen 26, being larger than the filament lumen 50 in one approach, provides a larger internal area for securing the filament 16, which is further described below. In one approach, the securement port 80 is disposed distally from the fluid entry ports 30, such that securing the filament 16 at the securement port 80 will have limited or no effect on proximal drainage flow through the catheter 10 after the fluid has entered the tube 14. However, the securement port 80 may also be disposed proximally from the ports 30 in another embodiment. The securement port 80 can also allow fluid to flow into the drainage lumen 26 in addition to the ports 30.

The end of the filament 16 that is opposite the proximal adjustable end 54 can be referred to as a distal secured end 82. The distal secured end 82 may include, in one approach, an enlarged head portion 84, illustrated in FIGS. 5 and 6A. The head portion 84 is larger or wider than the maximum width of the securement port 80. The head portion 84 is disposed within the tube 14, preferably the within the drainage lumen 26, but may be secured in another lumen, such as a filament lumen or other additional lumen.

The enlarged head portion 84 can be of any type that results in a head larger than the width of the securement port 80, such that it will not be pulled out through the securement port 80. Accordingly, the filament 16 is prevented from being pulled out of the tube 14 due to the interference between the head 84 and the securement port 80. Even if the filament 16 were to be ultimately pulled out of the exit port 40, the head 84, being inside the tube 14, will prevent the filament 16 from being fully pulled distally out of the catheter 10.

Figure 6A:
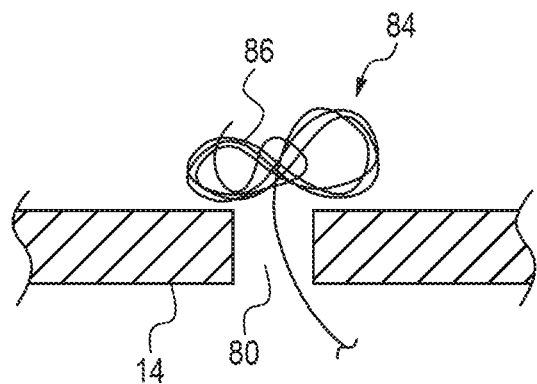
FIG. 6A is a partial cross-section view of a head portion of the filament at the distal end.

In one embodiment, as shown in FIG. 6A, the head portion 84 is in the form of a knot 86 of filament material, where the knot 86 is larger than the width of the securement port 80.

In another embodiment, as shown in FIG. 5, the head portion 84 is in the form of a "T-tip" 88. The T-tip 88 may be a separate piece that is tied to the end of the filament 16, or it may be crimped to the end of the filament 16, adhered to the end of the filament 16, or overmolded onto the end of the filament 16. It will be appreciated that other forms of attachment of the T-tip 88 to the filament 16 can also be used. The T-tip 88 has a width that is greater than the width of the securement port 80.

Figure 6B:
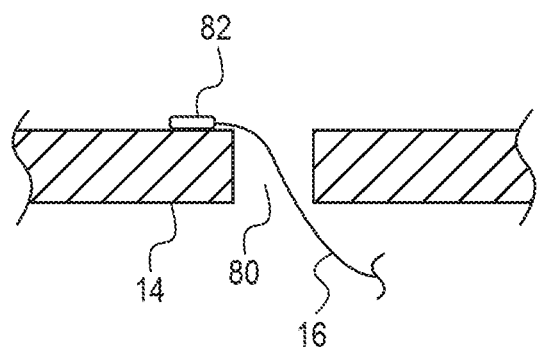
FIG. 6B is a partial cross-sectional view of the filament being bonded to an interior of the tube at the distal end.
Figure 6C:
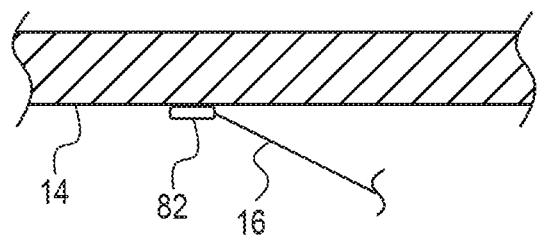
FIG. 6C is a partial cross-sectional view of the filament being bonded to an exterior of the tube at the distal end.

In another approach, as shown in FIG. 6B rather than use an enlarged head portion 84, the secured end 82 can be glued or otherwise adhered to the interior of the tube 14 near the securement port 80. Similarly, the secured end 82 can be embedded into the material of the tube 14. The secured end 82 can also be welded to the tube 14. In yet another approach, the secured end 82 can be fixed or secured to the outer surface of the tube 14 in a similar manner, as shown in FIG. 6C.

Thus, this embodiment includes the adjustable end 54 that extends proximally from the tube 14, and the adjustable end 54 can be manipulated and adjusted to place the filament 16 in tension to create the tight distal loop. The tension on the filament 16 will cause the distal end 22 of the tube 14 to slide along the filament 16 and be urged toward the secured end 82, thereby creating the loop.

The adjustable end 54 can extend through the hub 12 in a manner similar to the above. The hub 12 is not shown in FIGS. 5-6C for clarity. It can be retained in a tensioned and proximally retracted position via known methods of retention, or the above described retention mechanism 60 can be used. Thus, the above described embodiment with the distal secured end 82 provides a robust solution to prevent instances of the filament 16 being left behind in the body, even in instances where the tube 14 is cut.

The above described approach uses a dual lumen design with both the drainage lumen 26 and a separate filament lumen 50. However, the above described approach with the head portion 84 could also be used in a single lumen design. In this approach, there is no separate filament lumen. Rather, the filament 16 will extend through the drainage lumen 26 and out of the tube 14 at or near the distal tip of the tube 14. The filament 16 will turn back proximally toward the securement port 80 similarly to the above, or be attached to the outer surface of the tube 14 as described above. The filament 16 can include the same head portion 84, and the adjustable end 54 can be similarly adjustable to ultimately define the tight distal loop of the tube 14 when the adjustable end 54 of the filament 16 is retracted.

With reference to FIGS. 7-10, in another approach, the filament 16 may be attached or secured to the tube 14 substantially along the length of the tube 14. Accordingly, in the event the tube 14 is cut, the filament 16 that remains extending along the tube 14 does not become loose because of its attachment and securement to the tube 14.

Figure 7:
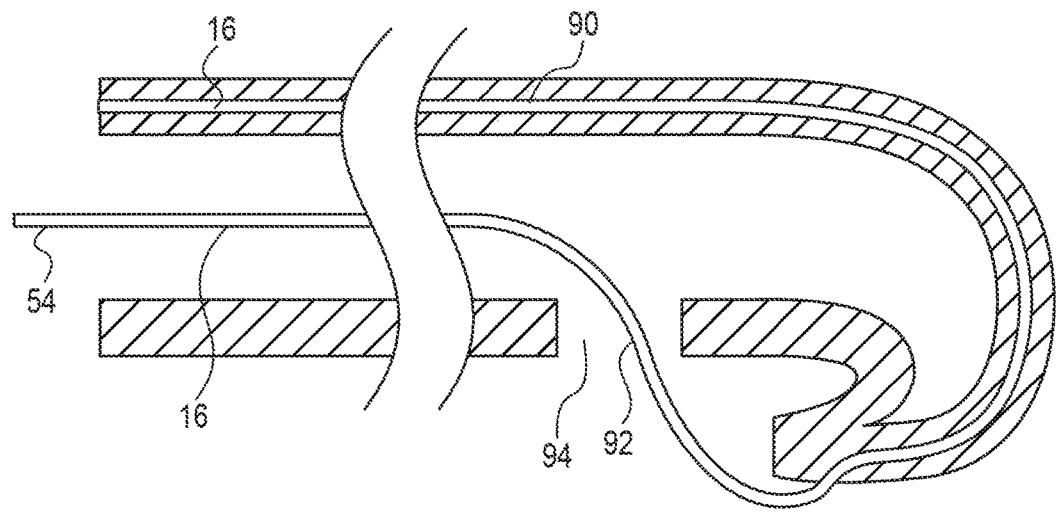
FIG. 7 is a schematic cross-sectional view of the filament embedded within a sidewall of the tube substantially along the length of the tube.
Figure 8:
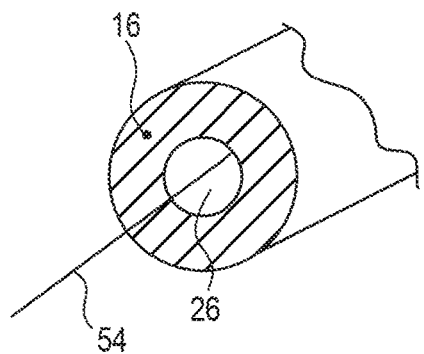
FIG. 8 is an end view of the tube illustrating the filament embedded in the tube.

In one embodiment, shown in FIGS. 7 and 8, the tube 14 includes the drainage lumen 26, but does not include a filament lumen. Rather, the filament 16 is co-extruded with the tube 14. In this form, the filament 16 remains embedded within the sidewall of the tube 14 along an embedded portion 90 of the filament 16. The filament 16 therefore does not include a fixed proximal end. Instead, a length of the filament 16 extending distally along the tube 14 is fixed, effectively defining a fixed portion. The filament 16 is therefore generally immobile relative to the tube 14 along the length in which it is embedded. A similar effect could be achieved by injecting an adhesive along a filament lumen with the filament 16 disposed therein. In either case, cutting the tube 14 at a location distal from the proximal end of the tube 14 will not cause the filament 16 to become loose, and the filament 16 will not be able to be separated from the tube 14.

At or near the distal end 22 of the tube 14, the filament 16 will extend out of the tube 14 such that the filament 16 is exposed from the tube 14 to define an adjustable portion 92 of the filament 16. The filament 16 will loop back proximally toward a filament entry port 94 disposed proximally from the point at which the filament 16 is exposed from the tube 14. The filament 16 will then enter the drainage lumen 26 through the entry port 94. The filament 16 will extend proximally though the drainage lumen 26, where the adjustable end 54 of the filament 16 is exposed for being adjusted by the user. In another approach, the filament 16 could re-enter the tube 14 and extend though an additional lumen instead of the drainage lumen 26.

Similar to the other embodiments described above, the adjustable end 54 of the filament 16 can be retracted to put the filament 16 in tension and define a loop at the distal end 22 of the tube 14. The adjustable end 54 of the filament 16 can then be secured and retained to maintain the loop. The adjustable end 54 can be secured via known retention methods, such as tying or crimping or clamping, or it can be attached to the retraction mechanism 60 described above.

Figure 9:
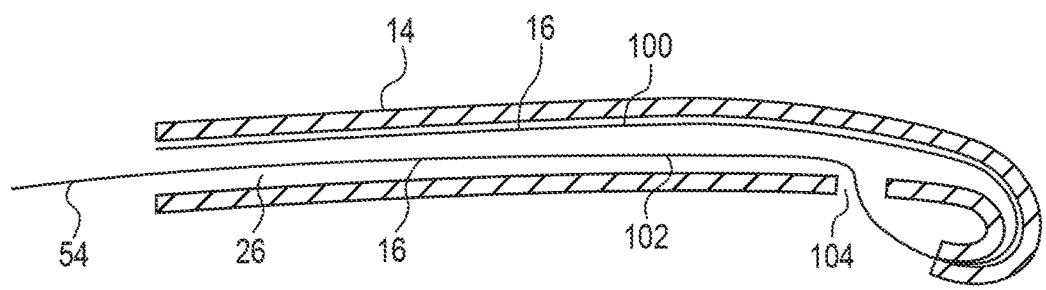
FIG. 9 is a schematic cross-sectional view of the filament bonded to an interior surface of the sidewall of the tube substantially along the length of the tube.
Figure 10:
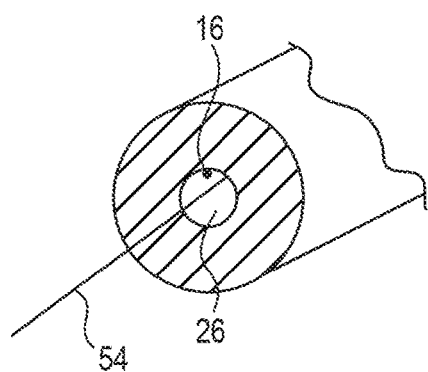
FIG. 10 is an end view of the tube illustrating the filament bonded to the interior surface of the sidewall of the tube.

In another approach, shown in FIGS. 9 and 10, rather than co-extrude the filament 16 along with the tube 14 such that the filament 16 is embedded in the wall of the tube 14, the filament 16 can instead be adhered to the inner surface of the drainage lumen 26. The filament 16 will extend through the drainage lumen 26 in a typical fashion, but the filament 16 will be bonded, welded, glued, or otherwise fixed to the inner surface of the drainage lumen 26. Thus, the filament 16 will be immobile relative to the tube 14 along the length that the filament 16 is fixed. This embodiment therefore includes a fixed length portion 100 of the filament 16.

Similar to the previous embodiment, the filament 16 also includes an adjustable portion 102. The adjustable portion 102 is the portion that is not attached to the tube 14. The adjustable portion 102 will extend from the tube 14 at or near the distal tip of the tube 14 and loop back proximally toward an entry port 104, where the filament 16 will enter the drainage lumen and extend proximally toward the proximal end of the catheter 10. The adjustable end 54 of the filament 16 will be adjustable to be retracted to place the filament 16 in tension and create the loop at the distal end 22 of the tube 14. The adjustable end 54 can then be secured and retained to maintain the loop via known methods or via the retraction mechanism 60 described above.

Thus, if the tube 14 is cut, the filament 16 will remain attached to the tube 14 via the remaining length of the fixed length portion 100 that is bonded or otherwise adhered to the tube 14.

The above described retraction mechanism 60 and, additionally or alternatively, the manners of preventing the filament 16 from being removed from the tube 14, provide a robust solution to instances of filaments being left behind after a procedure has been completed. The above described embodiments provide a failsafe and peace of mind to surgeons and other users that are involved with the placement and removal of drainage catheters.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

The invention claimed is:

1. A catheter having a proximal end and a distal end comprising:
a tube having a proximal end and a distal end and defining a first lumen and a second lumen extending therebetween, wherein the first lumen and the second lumen extend side-by-side along a length of the second lumen;
an exit port defined by the tube and extending through the first lumen of the tube adjacent the distal end of the tube;

an entry port extending through the second lumen of the tube and creating fluid communication between an exterior of the tube and the second lumen of the tube; and a filament extending within the first lumen of the tube and extending out of the exit port such that a portion of the filament is exposed to the exterior of the tube and further extending into the second lumen through the entry port;

wherein the filament includes a free end disposed at the proximal end, the free end being adjustable proximally and distally, wherein proximal retraction of the filament puts the filament in tension and creates a looped end portion of the tube where the exit port and entry port are urged toward each other, and releasing the filament from its proximal retraction allows the tube to return to a non-looped shape and the exit and entry ports to move away from each other;

wherein the filament is coupled to the tube to prevent the filament and tube from being separated in response to retraction of the tube.

2. The catheter of claim 1, wherein the filament includes a distal secured end that is coupled to the tube at the entry port.

3. The catheter of claim 2, wherein the free end is disposed at an opposite end of the filament from the distal secured end.

4. The catheter of claim 2, wherein the distal secured end is disposed within the second lumen of the catheter.

5. The catheter of claim 4, wherein the distal secured end includes a head portion having a width that is larger than a width of the entry port.

6. The catheter of claim 5, wherein the head portion is in a form of a T-tip.

7. The catheter of claim 1, wherein the filament includes a secured length portion that is secured to the tube along a length of the tube.

8. The catheter of claim 7, wherein the secured length portion is embedded in a sidewall of the tube.

9. The catheter of claim 7, wherein the secured length portion is disposed within the second lumen, and the secured length portion is bonded to an inner surface of the tube.

10. The catheter of claim 2, wherein the second lumen comprises a drainage lumen and the first lumen comprises a filament lumen, and the filament extends through the filament lumen and exits the filament lumen at the exit port.

11. The catheter of claim 7, wherein the filament includes an adjustable portion that extends proximally from the exit port through the first lumen.

12. A catheter system comprising:

a tube having a proximal end and a distal end and defining a first lumen and a second lumen extending therebetween, wherein the first lumen and the second lumen extend side-by-side along a length of the second lumen;

an exit port defined by the first lumen of the tube and extending through the first lumen of the tube adjacent the distal end of the tube;

an entry port extending through the second lumen of the tube and creating fluid communication between an exterior of the tube and the second lumen of the tube;

a filament extending within the first lumen of the tube and extending out of the exit port such that a portion of the filament is exposed to the exterior of the tube and further extending into the second lumen of the tube through the entry port;

wherein the filament includes a free end disposed at the proximal end, the free end being adjustable proximally and distally, wherein proximal retraction of the filament puts the filament in tension and creates a looped end portion of the tube where the exit port and entry port are urged toward each other, and releasing the filament from its proximal retraction allows the tube to return to a non-looped shape and the exit and entry ports to move away from each other;

wherein the filament is coupled to the tube to prevent the filament and tube from being separated in response to retraction of the tube; and a cam system coupled to the free end of the filament for adjusting the filament proximally and distally, the cam system moveable between a first fixed position and a second fixed position;

wherein the second fixed position places the filament in tension and is disposed proximally relative to the first fixed position.

* * * * *